US005859235A

United States Patent [19]
Liu et al.

[11] Patent Number: 5,859,235
[45] Date of Patent: Jan. 12, 1999

[54] DIPTERAN-ACTIVE URACIL DERIVATIVE

[75] Inventors: Chi-Li Liu, Davis; William D. Lidster; Carmen Sanchez Lopez, both of Sacramento, all of Calif.

[73] Assignee: Abbott Laboratories, Abbott Park, Ill.

[21] Appl. No.: 273,260

[22] Filed: Jul. 11, 1994

[51] Int. Cl.$^6$ .................. C07H 19/06; C07H 19/067; C07H 19/073
[52] U.S. Cl. ............... 536/28.53; 435/135; 435/136; 435/137; 435/72; 435/84; 435/87; 514/252; 514/264; 536/28.4; 536/28.5; 536/28.53
[58] Field of Search ................ 536/28.53, 28.54, 536/28.4, 28.5; 435/135, 136, 137, 72, 41, 84, 87; 514/252, 264

[56] References Cited

U.S. PATENT DOCUMENTS

| 4,437,877 | 3/1984 | Nagano et al. | 544/48 |
| 5,116,404 | 5/1992 | Ishii et al. | 514/252 |

FOREIGN PATENT DOCUMENTS

| 0 457 498 A2 | 5/1991 | European Pat. Off. . |
| 9409630 | 11/1994 | WIPO . |

OTHER PUBLICATIONS

Herrewege, Entomophage, vol. 15, pp. 200–222, 1970.
Hoffmann et al., Arch Microbiol, vol. 146, pp. 7–11, 1986.
Karamanlidou et al., Applied and Environmental Microbiology, vol. 57, No. 8, pp. 2277–2282, 1991.
Widner et al., Journal of Bacteriology, vol. 171, No. 2, pp. 965–974, 1989.
Levinson, Analytical Chemistry of *Bacillus thuringiensis*, pp. 114–135, 1990.
Levinson et al., Journal of Bacteriology, vol. 172, pp. 3172–3179, 1990.
Steinhause, Journal of Invertebrate Pathology, vol. 9, pp. 573–577, 1967.
Rigal et al., Genetica, vol. 81, pp. 215–228, 1990.
Marec et al., Journal of Invertebrate Pathology, vol. 53, pp. 347–353, 1989.
Carlberg et al., Journal of Invertebrate Pahtology, vol. 49, pp. 194–197, 1987.
Linnainmaa et al., Hereditas, vol. 85, pp. 113–122, 1977.
Sorsa et al., Hereditas, vol. 84, p. 253, 1976.
Nishiura, Journal of Invertebrate Pahtology, vol. 51, pp. 15–22, 1988.
Westman et al., Specialia, pp. 871–872, 1967.
Huston et al., Specialia, pp. 73–75, 1971.
Sidén et al., Journal of General Microbiology, vol. 114, pp. 45–52, 1979.
Argauer, R.J., et al., "Evidence for a Novel Insecticidally Active Exotoxin Produced by the HD 116 Strain of *Bacillus thuringiensis* var. morrison", *Journ of Entomological Sci*, 2:205–213 (1991).
Gardner, W.A., Enhanced Activity of Selected Combinations of *Bacillus thuringiensis* and Beta–Exotoxin Against Fall Armyworm (Lepidoptera: Noctuidae) Larvae, *Journ of Ecomomic Entomology*, 2:463–469 (1988).

*Primary Examiner*—Blaine Lankford
*Attorney, Agent, or Firm*—Cheryl H. Agris; Michael J. Ward

[57] ABSTRACT

The invention relates to a novel substance with activity against insect pests of the order Diptera. The invention further relates to the substance which acts together with a Bacillus related pesticide, a chemical pesticide and/or a virus with pesticidal properties. The invention further relates to a novel strain(s) of *Bacillus thuringiensis* which produces such a substance. The invention further relates to pesticidal compositions comprising the substance and a pesticidal carrier, or the substance and a Bacillus related pesticide, a chemical pesticide and/or a virus with pesticidal properties as well as methods of using the pesticidal compositions to control a pest.

5 Claims, 2 Drawing Sheets

DIPTERAN-ACTIVE URACIL DERIVATIVE

FIELD OF THE INVENTION

The invention relates to a novel compound with activity against an insect pest(s) of the order Diptera. The invention further relates to such a compound which potentiates or synergizes the pesticidal activity of a Bacillus related pesticide, a chemical pesticide and/or an entomopathogenic virus. The invention further relates to a novel strain(s) of *Bacillus thuringiensis* which produces such a compound. The invention further relates to pesticidal formulations comprising the compound and a pesticidal carrier, or the compound and a Bacillus related pesticide, a chemical pesticide and/or an entomopathogenic virus. The invention further relates to methods of using the pesticidal formulations to control a pest.

BACKGROUND OF THE INVENTION

Every year, pests detrimental to agriculture, forestry, and public health cause losses in the millions of dollars. Various strategies have been used to control such pests.

One strategy is the use of chemical pesticides with a broad range or spectrum of activity. However, there are a number of disadvantages with using chemical pesticides. Specifically, because of their broad spectrum of activity, these pesticides may destroy non-target organisms such as beneficial insects and parasites of destructive pests. Additionally, chemical pesticides are frequently toxic to animals and humans. Furthermore, targeted pests frequently develop resistance when repeatedly exposed to such substances.

Another strategy involves the use of biopesticides to control insect, fungal and weed infestations. Biopesticides are naturally occurring pathogens and/or the substances produced by these pathogens. The advantage of using biopesticides is that they are generally less harmful to non-target organisms and the environment as a whole compared to chemical pesticides.

The most widely used biopesticide is *Bacillus thuringiensis*. *Bacillus thuringiensis* is a motile, rod-shaped, gram-positive bacterium that is widely distributed in nature, especially in soil and insect-rich environments. During sporulation, *Bacillus thuringiensis* produces a parasporal crystal inclusion(s) which is insecticidal upon ingestion to susceptible insect larvae of the orders Lepidoptera, Diptera, and Coleoptera. The inclusions may vary in shape, number, and composition. They are comprised of one or more proteins called delta-endotoxins, which may range in size from 27–140 kDa. The insecticidal delta-endotoxins are generally converted by proteases in the larval gut into smaller (truncated) toxic polypeptides, causing midgut destruction, and ultimately, death of the insect (Höfte and Whiteley, 1989, *Microbiological Reviews* 53:242–255).

There are several *Bacillus thuringiensis* strains that are widely used as biopesticides in the forestry, agricultural, and public health areas. *Bacillus thuringiensis* subsp. kurstaki and *Bacillus thuringiensis* subsp. aizawai produce delta-endotoxins specific for Lepidoptera. A delta-endotoxin specific for Coleoptera is produced by *Bacillus thuringiensis* subsp. tenebrionis (Krieg et al., 1988, U.S. Pat. No. 4,766,203). Furthermore, *Bacillus thuringiensis* subsp. israelensis produces delta-endotoxins specific for Diptera (Goldberg, 1979, U.S. Pat. No. 4,166,112).

Other *Bacillus thuringiensis* strains specific for dipteran pests have also been described. A *Bacillus thuringiensis* isolate has been disclosed which is toxic to Diptera and Lepidoptera (Hodgman et al., 1993, *FEMS Microbiology Letters* 114:17–22). Sodium dodecyl polyacrylamide gel electrophoresis of the purified crystal delta-endotoxin from this isolate revealed three protein species which are related to CryIA(b), CryIB, and CryIIA toxins. There has also been disclosed a *Bacillus thuringiensis* isolate which produces a dipteran-active crystal comprised of proteins with molecular weights of 140, 122, 76, 72, and 38 kDa (Payne, 1994, U.S. Pat. No. 5,275,815). EPO 480,762 discloses five *B.t.* strains which are each active against dipteran pests; each also have a unique crystal delta-endotoxin pattern.

Several *Bacillus thuringiensis* strains have been described which have pesticidal activity against pests other then Lepidoptera, Coleoptera, and Diptera. Five *Bacillus thuringiensis* strains have been disclosed which produce delta-endotoxins that are toxic against nematodes (Edwards, Payne, and Soares, 1988, Eur. Pat. Appl. No. 0 303 426 B1). There has also been disclosed a *Bacillus thuringiensis* strain, PS81F, which can be used to treat humans and animals hosting parasitic protozoans (Thompson and Gaertner, 1991, Eur. Pat. Appl. No. 0 461 799 A2). Several *Bacillus thuringiensis* isolates have also been disclosed with activity against acaride pests. These isolates produce crystals comprised of proteins with molecular weights in the (wide) range of 35 kDa to 155 kDa (Payne, Cannon, and Bagley, 1992, PCT Application No. WO 92/19106). There have also been disclosed *Bacillus thuringiensis* strains with activity against pests of the order Hymenoptera (Payne, Kennedy, Randall, Meier, and Uick, 1992, Eur. Pat. Appl. No. 0 516 306 A2); with activity against pests of the order Hemiptera (Payne and Cannon, 1993, U.S. Pat. No. 5,262,159); with activity against fluke pests (Hickle, Sick, Schwab, Narva, and Payne, 1993, U.S. Pat. No. 5,262,399; and with activity against pests of the order Phthiraptera (Payne and Hickle, 1993, U.S. Pat. No. 5,273,746). Furthermore, another strain of *Bacillus thuringiensis* subsp. kurstaki, WB3S-16, isolated from Australian sheep wool clippings, has been disclosed that is toxic to the biting louse *Damalinia ovis*, a Phthiraptera pest (Drummond, Miller, and Pinnock, 1992, *J. Invert. Path.* 60:102–103).

The delta-endotoxins are encoded by cry (crystal protein) genes which are generally located on plasmids. The cry genes have been divided into six classes and several subclasses based on relative amino acid homology and pesticidal specificity. The major classes are Lepidoptera-specific (cryI); Lepidoptera-and Diptera-specific (cryII); Coleoptera-specific (cryIII); Diptera-specific (cryIV) (Höfte and Whiteley, 1989, *Microbiological Reviews* 53:242–255); Coleoptera- and Lepidoptera-specific (referred to as cryV genes by Tailor et al., 1992, *Molecular Microbiology* 6:1211–1217); and Nematode-specific (referred to as cryV and cryVI genes by Feitelson et al., 1992, *Bio/Technology* 10:271–275).

Delta-endotoxins have been produced by recombinant DNA methods. The delta-endotoxins produced by recombinant DNA methods may or may not be in crystal form.

Some strains of *Bacillus thuringiensis* have been shown to produce a heat-stable pesticidal adenine-nucleotide analog, known as β-exotoxin type I or thuringiensin, which is pesticidal alone (Sebesta et al., in H. D. Burges (ed.), *Microbial Control of Pests and Plant Diseases*, Academic Press, New York, 1980, pp. 249–281). β-exotoxin type I has been found in the supernatant of some *Bacillus thuringiensis* cultures. It has a molecular weight of 701 and is comprised of adenosine, glucose, and allaric acid (Farkas et al., 1977, *Coll. Czechosslovak Chem. Comm.* 42:909–929; Lüthy et al., in Kurstak (ed.), *Microbial and Viral Pesticides,* Marcel Dekker, New York, 1982, pp. 35–72). Its host range includes, but is not limited to, *Musca domestica, Mamestra configurata* Walker, *Tetranychus urticae, Drosophila melanogaster;* and *Tetranychus cinnabarinus.* The toxicity of β-exotoxin type I is thought to be due to inhibition of DNA-directed RNA polymerase by competition with ATP. It has been shown that β-exotoxin type I is encoded by a cry plasmid in five *Bacillus thuringiensis* strains (Levinson et al., 1990, *J. Bacteriol.* 172:3172–3179). β-exotoxin type I was found to be produced by *Bacillus thuringiensis* subsp. thuringiensis serotype 1, *Bacillus thuringiensis* subsp. tolworthi serotype 9, and *Bacillus thuringiensis* subsp. darmstadiensis serotype 10.

Another β-exotoxin classified as β-exotoxin type II has been described (Levinson et al., 1990, *J. Bacteriol.* 172:3172–3179). β-exotoxin type II was found to be produced by *Bacillus thuringiensis* subsp. morrisoni serotype 8ab and is active against *Leptinotarsa decemlineata.* The structure of β-exotoxin type II is not completely known, but is significantly different from that of β-exotoxin type I in that a pseudouridine moiety is in the place of adenine in which attachment to the ribose ring is at a position that would otherwise be occupied by a proton (Levinson, in Hickle and Finch (eds.), *Analytical Chemistry of Bacillus thuringiensis*, ACS Symposium Series, Washington, D.C., 1990, pp. 114–136). Furthermore, there is only one signal in the proton NMR spectrum corresponding to the nucleoside base (at 7.95 ppm), and does not have a ribose-type anomeric protein signal (5.78 ppm).

Other water soluble substances that have been isolated from *Bacillus thuringiensis* include alpha-exotoxin which is toxic against the larvae of *Musca domestica* (Luthy, 1980, *FEMS Microbiol. Lett.* 8:1–7); gamma-exotoxins, which are various enzymes including lecithinases, chitinases, and proteases, the toxic effects of which are expressed only in combination with beta-exotoxin or delta-endotoxin (Forsberg et al., 1976, *Bacillus thuringiensis: Its Effects on Environmental Quality,* National Research Council of Canada, NRC Associate Committee on Scientific Criteria for Environmental Quality, Subcomittees on Pesticides and Related Compounds and Biological Phenomena); sigma exotoxin which has a structure similar to beta-exotoxin, and is also active against *Leptinotarsa decemlineata* (Argauer et al., 1991, *J. Entomol. Sci.* 26:206–213); and anhydrothuringiensin (Prystas et al., 1975, *Coll. Czechosslovak Chem. Comm.* 40:1775).

WO 94/09630 discloses a factor that potentiates the pesticidal activity of *B.t.*. This factor is obtained from the supernatant of a *B.t.* culture.

The art has strived to improve the effectiveness and to broaden the host range of *Bacillus thuringiensis.* Means have included isolating *Bacillus thuringiensis* strains with improved or new pesticidal activity, engineering present *Bacillus thuringiensis* strains, and designing more effective formulations by combining *Bacillus thuringiensis* crystal delta-endotoxins and spores with new pesticidal carriers or with chemical pesticides.

It is an object of the present invention to provide a novel substance with activity against pests of the order Diptera.

It is also an object of the present invention to improve the pesticidal activity of known *Bacillus thuringiensis* formulations.

It is a further object of the present invention to enhance the pesticidal activity of pesticides.

It is advantageous to isolate new strains of *Bacillus thuringiensis* to produce new substances, so there exists a broader spectrum of biopesticides for use against any given insect pest.

SUMMARY OF THE INVENTION

The invention relates to a novel substance characterized by having the following properties:

(a) pesticidal activity against an insect pest of the order Diptera; and (b) acts together, e.g. as a potentiator or synergizer with a different Bacillus related pesticide, a chemical pesticide, and/or an entomopathogenic virus against a pest(s).

The substance of the invention may also have a uracil nucleoside having three sugar moieties and two phosphates with $^1$H-NMR chemical shifts at about 7.62 (1H,d), 5.83 (1H,d), and 5.78 (1H,d). The substance may have a molecular weight of less than about 1000.

The substance may be obtainable from a Bacillus fermentation. Alternatively, the substance may be obtainable from a fermentation of a strain of Bacillus, e.g. *Bacillus thuringiensis,* wherein essentially all of the pesticidal activity of the strain is in the supernatant of the fermentation. Specifically, the substance of the present invention has an $LC_{50}$ of 7 μg of active ingredient/g diet against *Musca domaestica* larvae as assayed by bioassay ($LC_{50}$ is the concentration of a given pesticidal substance required to kill 50% of the pests). The $LC_{50}$ of the pellet of the fermentation of said strain is more than about 3000 μg of active ingredient/g diet against *Musca domestica* larvae as assayed by bioassay.

The substance of the present invention may have pesticidal activity against an insect pest of the genus Drosophila and the genus Musca of the order Diptera. In a most specific embodiment, the substance of the present invention has pesticidal activity against an insect pest of the species *Drosophila melanogaster* and the species *Musca domestica* of the order Diptera. In another embodiment, the substance of the present invention potentiates the pesticidal activity of a Bacillus related pesticide. In a specific embodiment, the substance of the present invention potentiates the insecticidal activity of *Bacillus thuringiensis* crystal delta-endotoxin(s) against an insect pest(s). In another embodiment, the substance of the present invention potentiates or synergizes the insecticidal activity of the *Bacillus thuringiensis* subsp. kurstaki crystal delta-endotoxin against an insect pest of the order Lepidoptera.

As defined herein, "a Bacillus related pesticide" is a Bacillus (e.g., *Bacillus thuringiensis* or *Bacillus subtilis*) strain, spore, or substance, e.g., protein or fragment thereof, with activity against or which kill pests or provides plant protection against a pest; or a microorganism capable of expressing a Bacillus gene encoding a Bacillus protein or fragment thereof with activity against or which kills pests or provides plant protection against a pest (e.g., *Bacillus thuringiensis* delta-endotoxin), and an acceptable carrier. The pest may be, for example, an insect, a nematode, a mite, or a snail. A microorganism, capable of expressing a Bacillus gene encoding a Bacillus protein or fragment thereof with activity against or which kill pests or provides plant protection against a pest, inhabits the phylloplane (the surface of the plant leaves), and/or the rhizosphere (the soil surrounding plant roots), and/or aquatic environments, and is capable of successfully competing in the particular environment (crop and other insect habitats) with the wild-type microorganisms and provide for the stable maintenance and expression of a Bacillus gene encoding a Bacillus protein or fragment thereof with activity against or which kill pests. Examples of such microorganisms include, but are not limited to, bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes, and Clostridium; algae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae; and fungi, particularly yeast, e.g., genera Saccharomyces, Cryptococcus, Kluyveromyces, Sporobolomyces, Rhodotorula, and Aureobasidium.

As defined herein "pesticidal activity" measures the amount of activity against a pest through killing or stunting of the growth of the pest or protecting the plant from pest infestation.

The invention further relates to a novel Bacillus and, specifically, a *Bacillus thuringiensis* strain(s) which produces such a substance. Crystal delta-endotoxin and spores obtained from a fermentation of a *Bacillus thuringiensis* strain of the present invention do not possess essentially any pesticidal activity. In a specific embodiment, the strain is selected from the group consisting of EMCC-0110 having the identifying characteristics of NRRL B-21269, or mutants and variants thereof having substantially the same properties of EMCC-0110, EMCC-0111 having the identifying characteristics of NRRL B-21270, or mutants and variants thereof having substantially the same properties of EMCC-0111, EMCC-0112 having the identifying characteristics of NRRL B-21271, or mutants and variants thereof having substantially the same properties of EMCC-0112, and EMCC-0113 having the identifying characteristics of NRRL B-21272, or mutants and variants thereof having substantially the same properties of EMCC-0113. The mutants and variants of EMCC-0110, EMCC-0111, EMCC-0112, and EMCC-0113 retain the ability to produce the substance of the present invention.

The invention further relates to a mutant or variant Bacillus strain wherein such a substance is obtained in a greater quantity compared to the parental strain as well as methods for obtaining such a mutant or variant.

The invention further relates to pesticidal compositions comprising the substance and a pesticidal carrier as well as the substance and a Bacillus related pesticide, chemical pesticide and/or an entomopathogenic virus as well as methods of using the pesticidal compositions to control a pest.

The invention is further directed to a method for obtaining "substantially pure" substance of the present invention comprising the steps of (a) culturing a Bacillus strain on a suitable growth medium;

(b) recovering the supernatant of (a); and (c) isolating the substance from the supernatant of (b) to obtain substantially pure substance.

As defined herein, a "substantially pure" substance means a substance which contains less than 5% of contaminants, for example, delta-endotoxin protein.

BRIEF DESCRIPTION OF THE FIGURES

These and other features, aspects, and advantages of the present invention will become better understood with regard to the following description, appended claims, and accompanying figures where:

DETAILED DESCRIPTION OF THE INVENTION

Obtaining the Substance

Figure 1:
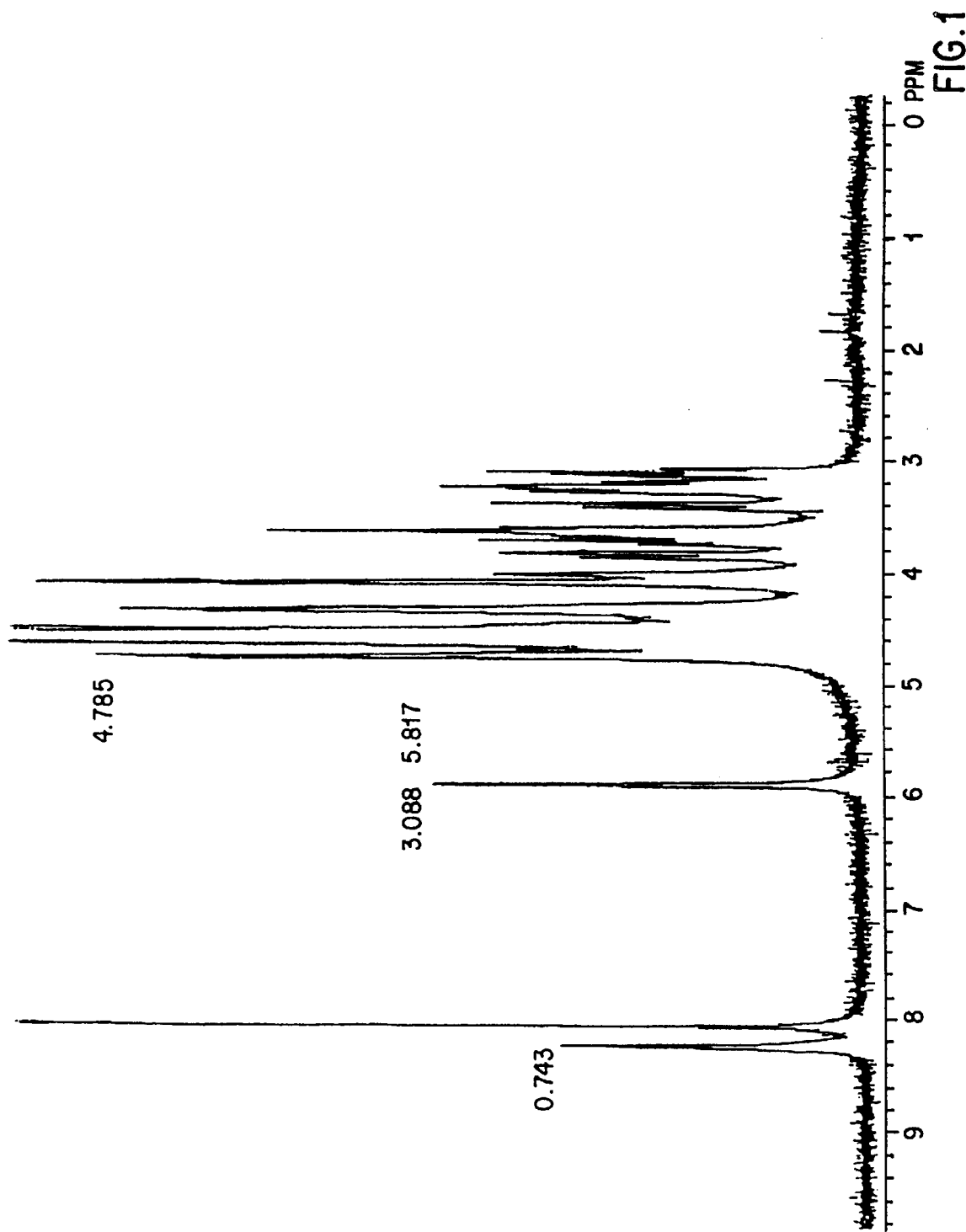
FIG. 1 is a $^1$H-NMR spectrum of the substance of the present invention.
Figure 2:
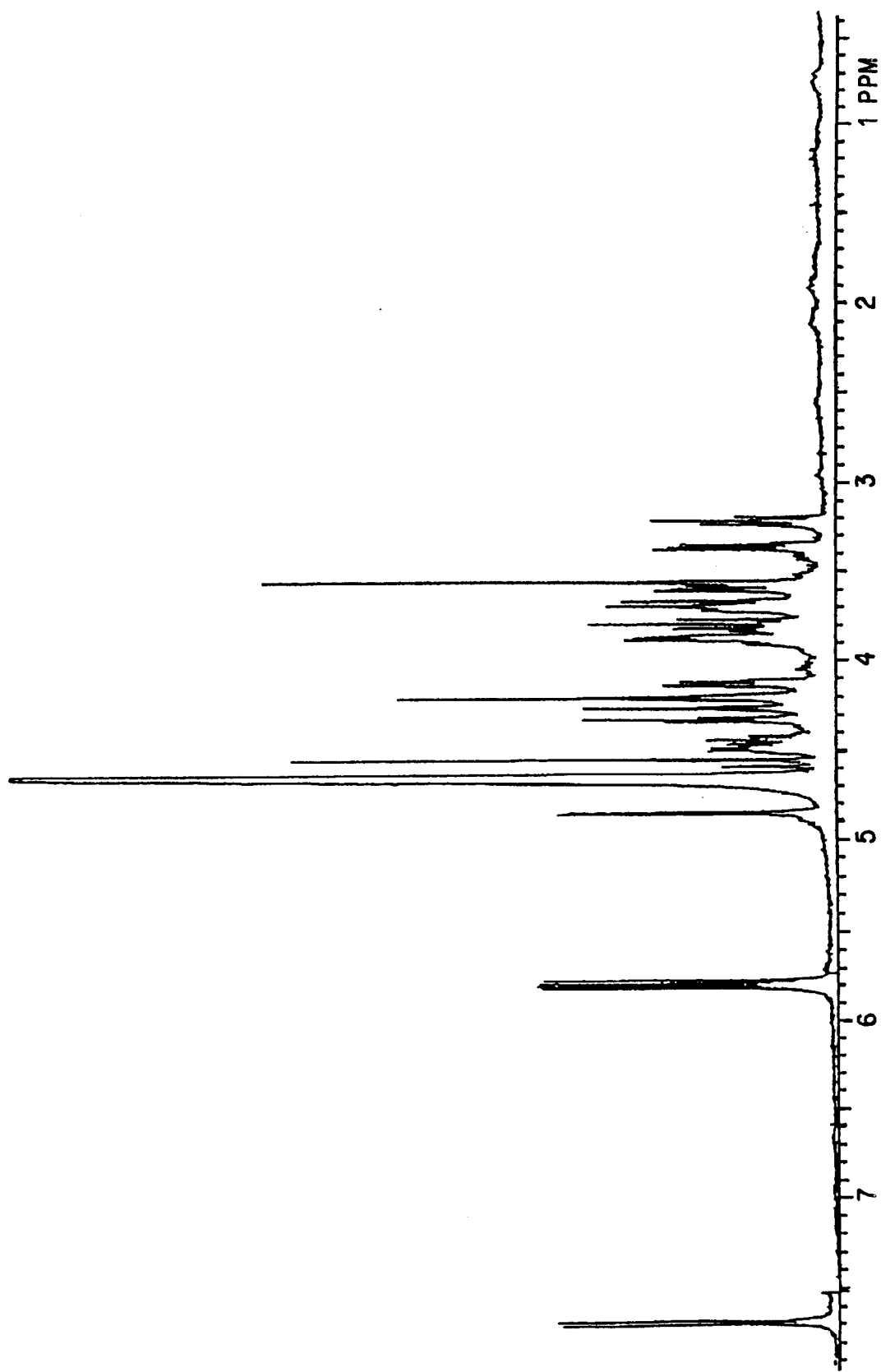
FIG. 2 is a $^1$H-NMR spectrum of β-exotoxin.

The substance of the present invention is produced by microorganisms belonging to the genus Bacillus, e.g. *Bacillus thuringiensis,* and is obtainable by culturing the Bacillus and recovering the substance from the supernatant. In a specific embodiment, the substance of the present invention is obtained from the supernatant of a fermentation of a *Bacillus thuringiensis* strain from the group consisting of EMCC-0110 having the identifying characteristics of NRRL B-21269, or mutants and variants thereof having substantially the same properties of EMCC-0110, EMCC-0111 having the identifying characteristics of NRRL B-21270, or mutants and variants thereof having substantially the same properties of EMCC-0111, EMCC-0112 having the identifying characteristics of NRRL B-21271, or mutants and variants thereof having substantially the same properties of EMCC-0112, and EMCC-0113 having the identifying characteristics of NRRL B-21272, or mutants and variants thereof having substantially the same properties of EMCC-0113. Mutants and variants of EMCC-0110, EMCC-0111, EMCC-0112, and EMCC-0113 retain the ability to produce the substance of the present invention.

In one embodiment, the substance of the present invention is obtained from a mutant or variant Bacillus, particularly, a mutant or variant *Bacillus thuringiensis,* wherein the substance is produced in a greater quantity, or a mutant or variant *Bacillus thuringiensis* wherein the insecticidal activity of the substance obtained from the mutant or variant is greater, as compared to the parental strain. A "parental strain" as defined herein is the original Bacillis strain before mutagenesis. To obtain such mutants or variants, the parental strain may, for example, be treated with a mutagen by chemical means such as N-methyl-N'-nitro-N-nitrosoguanidine or ethylmethane-sulfonate, or by irradiation with gamma-rays, X-rays, or UV. Specifically, in one method of mutating Bacillus strains and selecting such mutants or variants, the following procedure is used:

i) the parental strain is treated with a mutagen;

ii) the thus presumptive mutants or variants of the parental strain are grown in a medium suitable for selection of a mutant strain; and iii) the mutant or variant strain is selected for increased production of the substance.

According to a preferred embodiment of this method, the selected colonies are grown in a production medium, and a final selection for mutant or variant strains capable of increased production of the substance is performed. Increased production can be determined by methods known in the art, e.g., high performance liquid chromatography, capillary electrophoresis, or thin layer chromatography.

Bacillus may be cultured using media and fermentation techniques known in the art (see, for example, Rogoff et al., 1969, *J. Invertebrate Path.* 14:122–129; Dulmage et al., 1971, *J. Invertebrate Path.* 18:353–358; Dulmage et al., in *Microbial Control of Pests and Plant Diseases,* H. D. Burges (ed.), Academic Press, New York, 1980). Upon completion of the fermentation cycle, the supernatant can be recovered by separating *Bacillus thuringiensis* spores and crystals from the fermentation broth by means well known in the art, e.g., centrifugation and/or ultrafiltration. The substance of the present invention is contained in the supernatant which may be recovered by means well known in the art, e.g., ultrafiltration, evaporation, and spray-drying.

Purification of the substance of the present invention can be carried out by various procedures known in the art including, but not limited to, chromatography (e.g., ion exchange, affinity, and size exclusion column chromatography), electrophoretic procedures, differential solubility, extraction, or any other standard technique known in the art (see, for example, *CRC Handbook of Natural Pesticides: Methods,* Volume II, Isolation and Identification, N. Bhushan Mandava, ed., CRC Press, Inc., Boca Raton, Fla., 1985).

The activity of the substance of the present invention may be bioassayed using procedures known in the art, such as artificial diet incorporation, artificial diet overlay, leaf painting, leaf dip, foliar spray, and aquatic. Specific examples of such bioassays are given in the Examples section, infra.

Compositions Comprising the Substance

The substance of the present invention can be formulated alone; with a Bacillus related pesticide, which as defined, supra, is a Bacillus strain, spore, protein or fragment, or other substance, thereof, with activity against or which kills pests or protects plants against a pest; with a chemical pesticide and/or an entomopathogenic virus and an acceptable carrier into a pesticidal composition(s), that is, for example, a suspension, a solution, an emulsion, a dusting powder, a dispersible granule, a wettable powder, an emulsifiable concentrate, an aerosol or impregnated granule. Examples of such Bacillus strains include, but are not limited to, *Bacillus thuringiensis* subsp. kurstaki (marketed as DIPEL™ from Abbott Laboratories, Inc., JAVELIN™ from Sandoz, BIOBIT™ from Novo Nordisk A/S, FORAY™ from Novo Nordisk A/S, BIOCOT™ from Novo Nordisk A/S, MVP™ from Mycogen, BACTOSPEINE™ from Novo Nordisk A/S, and THURICIDE™ from Sandoz); *Bacillus thuringiensis* subsp. aizawai (marketed as FLORBAC™ from Novo Nordisk A/S, and XENTARI™ from Abbott Laboratories, Inc.); *Bacillus thuringiensis* subsp. tenebrionis (marketed as NOVODOR™ from Novo Nordisk A/S, TRIDENT™ from Sandoz, M-TRAK™ and M-ONE™ from Mycogen, and DITERRA™ from Abbott Laboratories Inc.); *Bacillus thuringiensis* subsp. israelensis (marketed as either BACTIMOS™ or SKEETAL™ from Novo Nordisk A/S, TEKNAR™ from Sandoz, and VECTOBAC™ from Abbott Laboratories, Inc.); *Bacillus thuringiensis kurstakiltenebrionis* (marketed as FOIL™ from Ecogen); *Bacillus thuringiensis kurstakilaizawai* (marketed as CONDOR™ from Ecogen and AGREE™ from Ciba-Geigy); and *Bacillus thuringiensis kurstakilkurstaki* (marketed as CUTLASS™ from Ecogen). The Bacillus related protein may be selected from the group including, but not limited to, CryI, CryII, CryIII, CryIV, CryV, and CryVI. The chemical pesticide may be, for example, an insect growth regulator such as diflubenzuron, a carbamate such as thiodicarb and methomyl, an organophosphate such as chlorpyrifos, a pyrethroid such as cypermethrin and esfenvalerate, inorganic fluorine such as cryolite, and a pyrrole. The entomopathogenic virus may be a baculovirus, e.g., *Autographa californica* nuclear polyhedrosis virus (NPV), *Syngrapha falcifera* NPV, *Cydia pomonella* GV (granulosis virus), *Heliothis zea* NPV, *Lymantria dispar* NPV, *Orgyia pseudotsugata* NPV, *Spodoptera exigua* NPV, *Neodiprion lecontei* NPV, *Neodiprion sertifer* NPV, *Harrisina brillians* NPV, and *Endopiza viteana* Clemens NPV.

The substance of the present invention may also be formulated with other factors or substances obtained from the supernatant of a Bacillus including, but not limited to, an exotoxin and/or the enhancing factor disclosed in WO94/09630 (U.S. application Ser. No. 08/146,852, filed Nov. 3, 1993), and/or substance disclosed in application Ser. No. 08/212,462, filed Mar. 14, 1994, incorporated herein by reference. Optionally, the formulation may also comprise a Bacillus related pesticide, chemical pesticide and/or a virus with pesticidal properties and an acceptable carrier.

In a specific embodiment, the components of said composition may act in a synergistic fashion. Said composition may therein have greater efficacy than can be attained with each individual component. Synergism may be manifested by equal or greater efficacy with lower and/or less frequent doses than would be required for each individual component. Alternatively, the substance of the present invention may act to potentiate a Bacillus related pesticide wherein the substance of the present invention may have no pesticidal activity by itself.

In compositions comprising the substance and a Bacillus related pesticide, the substance may be present in the amount of at least about 0.1 g/BIU or 0.05 g factor per g Bacillus delta-endotoxin and spore, optionally to about 300 g/BIU or 150 g substance per g Bacillus delta-endotoxin and spore, preferably 2 g/BIU or 1 g substance per g Bacillus delta-endotoxin and spore. As defined herein "BIU" is billion international units as determined by bioassay. The bioassay compares the sample to a standard Bacillus reference material using *Trichoplusia ni* or other pest as the standard test insect. The potency is determined by dividing the reference standard $LC_{50}$ then multiplying by the reference standard potency.

In another embodiment, the composition may comprise the substance of the present invention in substantially pure form or a supernatant from Bacillus in dry, concentrated, or liquid form and a suitable pesticidal carrier, examples of which are disclosed, infra. This composition may be applied separately to a plant, e.g., transgenic plants. Specifically, the composition may be applied to a plant previously containing and expressing a *Bacillus thuringiensis* gene. In another embodiment, the composition may be applied to a plant previously exposed to a *Bacillus thuringiensis* composition. In another embodiment, the composition may be applied to other environments of a dipteran pest(s), e.g., water or soil. The substance is present in the composition at a concentration of about 0.001% to about 60% (w/w).

The composition comprising the substance and a pesticidally acceptable carrier in addition to controlling a pest may also be used to decrease the resistance of a pest to a pesticide. Alternatively, the composition may be used to potentiate a Bacillus related pesticide. The composition in one embodiment may be applied at the same time as the pesticide in an amount of at least about 2 g substance/BIU up to optionally about 300 g substance/BIU. In another embodiment, the composition may be applied up to about 24 hours after the pesticide as an adjuvant to extend the efficacy of residual pesticide.

Such compositions disclosed above may be obtained by the addition of a surface active agent, an inert carrier, a preservative, a humectant, a feeding stimulant, an attractant, an encapsulating agent, a binder, an emulsifier, a dye, a U.V. protectant, a buffer, a flow agent, or other component to facilitate product handling and application for particular target pests.

Suitable surface-active agents include anionic compounds such as a carboxylate, for example, a metal carboxylate of a long chain fatty acid; a N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates; salts of sulphonated phenol-formaldehyde condensates; or more complex sulphonates such as the amide sulphonates, e.g., the sulphonated condensation product of oleic acid and N-methyl taurine or the dialkyl sulphosuccinates, e.g., the sodium sulphonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include inorganic minerals such as kaolin, mica, gypsum, fertilizer, phyllosilicates, carbonates, sulfates, or phosphates; organic materials such as sugar, starches, or cyclodextrins; or botanical materials such as wood products, cork, powdered corncobs, rice hulls, peanut hulls, and walnut shells.

The compositions of the present invention can be in a suitable form for direct application or as a concentrate or primary composition which requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 pound to 5.0 pounds per acre when in dry form and at about 0.01 pint to 25 pints per acre when in liquid form.

In a further embodiment, the *Bacillus thuringiensis* crystal delta-endotoxin and/or substance of the present invention can be treated prior to formulation to prolong the pesticidal activity when applied to the environment of a target pest as long as the pretreatment is not deleterious to the crystal delta-endotoxin or substance. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; and histological fixatives, such as Bouin's fixative and Helly's fixative (see, for example, Humason, *Animal Tissue Techniques,* W. H. Freeman and Co., 1967).

The compositions of the invention can be applied directly to the plant by, for example, spraying or dusting at the time when the pest has begun to appear on the plant or before the appearance of pests as a protective measure. Plants to be protected within the scope of the present invention include, but are not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes), lauraceae (avocados, cinnamon, camphor), deciduous trees and conifers (linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals. The composition can be applied by foliar, furrow, broadcast granule, "lay-by", or soil drench application. It is generally important to obtain good control of pests in the early stages of plant growth as this is the time when the plant can be most severely damaged. The spray or dust can conveniently contain another pesticide if this is thought necessary. In a preferred embodiment, the composition of the invention is applied directly to the plant.

The compositions of the present invention can also be applied directly to ponds, lakes, streams, rivers, still water, and other areas subject to infestation by dipteran pests, especially pests of concern to public health. The composition can be applied by spraying, dusting, springling, or the like.

The compositions of the present invention may be effective against insect pests of the order Diptera, e.g., *Aedes sp., Andes vittatus, Anastrepha ludens, Anastrepha suspensa, Anopheles barberi, Anopheles quadrimaculatus, Armigeres subalbatus, Calliphora stygian, Calliphora vicina, Ceratitis capitata, Chironomus tentans, Chrysomya rufifacies, Cochliomyia macellaria, Culex sp., Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina morsitans morsitans, Glossina moristans submorsitans, Glossina pallidipes, Glossina palpalis gambiensis, Glossina palpalis palpalis, Glossina tachinoides, Haemagogus equinus, Haematobia irritans, Hypoderma bovis, Hypoderma lineatum, Leucopis ninae, Lucilia cuprina, Lucilia sericata, Lutzomyia longlpaipis, Lutzomyia shannoni, Lycoriella mali, Mayetiola destructor, Musca autumnalis, Musca domestica, Neobellieria sp., Nephrotoma suturalis, Ophyra aenescens, Phaenicia sericata, Phlebotomus sp., Phornia regina, Sabethes cyaneus, Sarcophaga bullata, Scatophaga stercoraria, Stomoxys calcitrans, Toxorhynchites amboinensis, Tripteroides bambusa*. However, the compositions of the invention may also be effective against insect pests of the order Lepidoptera, e.g., *Achroia grisella, Acleris gloverana, Acleris variana, Adoxophyes orana, Agrotis ipsilon, Alabama argillacea, Alsophila pornetaria, Anmyelois transitella, Anagasta kuehniella, Anarsia lineatella, Anisota senatoria, Antheraea pernyi, Anticarsia gemmatalis, Archips sp., Argyrotaenia sp., Athetis mindara, Bombyx mori, Bucculatrix thurberiella, Cadra cautella, Choristoneura sp., Cochylis hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola, Eupoecilia ambiguella, Euproctis chrysorrhoea, Euxoa messoria, Galleria mellonella, Grapholita molesta, Harrisina americana, Helicoverpa* subflexa, Helicoverpa zea, Heliothis virescens, Hemileuca oliviae, Homoeosoma electellun, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis, Malacosoma sp., Mamestra brassicae, Mamestra configurata, Manduca quinquemaculata, Manduca sexta, Maruca testulalis, Melanchra picta, Operophtera brumata, Orgyia sp., Ostrinia nubilalis, Paleacrita vernata, Papilio cresphontes, Pectinophora gossypiella, Phlyganidia califorimica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana, Spodoptera sp., Thaurnstopoea pityocampa, Tineola bisselliella, Trichoplusia ni, Udea rubigalis, Xylomyges curialis, Yponomeuta padella; Coleoptera, e.g., Leptinotarsa sp., Acanthoscelides obtectus, Callosobruchus chinensis, Epilachna varivestis, Pyrrhalta luteola, Cylas formicarius elegantulus, Listronotus oregonensis, Sitophilus sp., Cyclocephala borealis, Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneun, Tribolium confusum, Tribolius destructor; Acari, e.g., Oligonychus pratensis, Panonychus ulmi, Tetranychus urticae; Hymenoptera, e.g., Iridomyrmex humilis, Solenopsis invicta; Isoptera, e.g., Reticulitermes hesperus, Reticulitermes flavipes, Coptotermes formosanus, Zootermopsis angusticollis, Neotermes connexus, Incisitermes minor, Incisitermes immigrans; Siphonaptera, e.g., Ceratophyllus gallinae, Ceratophyllus niger, Nosopsyllus fasciatus, Leptopsylla segnis, Ctenocephalides canis, Ctenocephalides felis, Echicnophaga gallinacea, Pulex irritans, Xenopsylla cheopis, Xenopsylla vexabilis, Tunga penetrans; and Tylenchida, e.g., Melodidogyne incognita, Pratylenchus penetrans.

In a specific embodiment, the compositions of the invention are active against insect pests of the genus Drosophila (e.g., *Drosophila melanogaster*) or the genus Musca (e.g., *Musca domestica*) of the order Diptera. The following examples are presented by way of illustration, not by way of limitation.

EXAMPLES

EXAMPLE 1

Cultivation of *Bacillus thuringiensis* isolates

Subcultures of *Bacillus thuringiensis* isolates EMCC-0110, EMCC-0111, EMCC-0112, and EMCC-0113, maintained on Nutrient Broth agar slants, are used to inoculate 250 ml baffled shake flasks containing 50 ml of medium with the following composition:

| | |
|---|---|
| Corn Steep Liquor | 15 g/L |
| Maltrin-100 | 40 g/L |
| Potato Starch | 30 g/L |
| KH$_2$PO$_4$ | 1.77 g/L |
| K$_2$HPO$_4$ | 4.53 g/L |

The pH of the medium is adjusted to 7.0 with 10N NaOH.

After inoculation, the shake flasks are incubated at 30° C. on a rotary shaker at 250 rpm for 72 hours until sporulation and cell lysis is observed microscopically releasing the crystals and spores. Crystals and spores are harvested from the whole culture broth by centrifugation at 15,000 rpm (Sorvall GSA rotor). The resulting supernatant is also recovered and filtered through a 0.2µ membrane before use. The whole culture broth, obtained in the above fermentation, as well as supernatant and crystals plus spores, are used to characterize the substance responsible for insecticidal activity.

EXAMPLE 2

Characteristics of *Bacillus thuringiensis* isolates

The dipteran-active *Bacillus thuringiensis* isolates EMCC-0110, EMCC-0111, EMCC-0112, and EMCC-0113 have the following characteristics:

Isolate EMCC-0110:
  Colony morphology: Large colony, dull surface, typical *Bacillus thuringiensis*
  Vegetative cell morphology: Typical *Bacillus thuringiensis*
  Inclusions: Phase bright bipyramidal inclusions Isolate EMCC-0111:
  Colony morphology: Large colony, dull surface, typical *Bacillus thuringiensis*
  Vegetative cell morphology: Typical *Bacillus thuringiensis*
  Inclusions: Phase bright medium size bipyramidal inclusions Isolate EMCC-0112:
  Colony morphology: Large colony, dull surface, typical *Bacillus thuringiensis*
  Vegetative cell morphology: Typical *Bacillus thuringiensis*
  Inclusions: Phase bright bipyramidal inclusions, but the edges are not as sharp as those of the bipyramidal inclusions from isolate EMCC-0111

Isolate EMCC-0113:
  Colony morphology: Large colony, dull surface, typical *Bacillus thuringiensis*
  Vegetative cell morphology: Typical *Bacillus thuringiensis*
  Inclusions: Phase bright spherical and tear-shaped inclusions

EXAMPLE 3

SDS-PAGE analysis of crystal inclusions of *Bacillus thuringiensis* isolates

The proteins comprising the crystal inclusions produced by *Bacillus thuringiensis* isolates EMCC-0110, EMCC-0111, EMCC-0112, and EMCC-0113 are determined by sodium dodecyl sulfate (SDS) polyacrylamide gel electrophoresis (PAGE). Before SDS-PAGE analysis of the crystal proteins, the crystals are separated from the spores by biphasic extraction with sodium dextran sulfate and polyethylene glycol.

Subcultures of *Bacillus thuringiensis* isolates EMCC-0110, EMCC-0111, EMCC-0112, and EMCC-0112, maintained on Nutrient Broth agar slants, are used to inoculate 250 ml baffled shake flasks containing 50 ml of medium with the following composition:

| | |
|---|---|
| D-Glucose | 2.0 g/L |
| Sodium Citrate | 2.0 g/L |
| CaCl$_2$ | 0.1 g/L |
| MnCl$_2$.4H$_2$O | 0.016 g/L |
| MnCl$_2$.6H$_2$O | 0.43 g/L |
| ZnCl$_2$ | 0.007 g/L |
| FeCl$_3$ | 0.003 g/L |
| Casamino acids | 5.0 g/L |
| KH$_2$PO$_4$ | 0.86 g/L |
| K$_2$HPO$_4$ | 0.55 g/L |

After inoculation, the shake flasks are incubated at 30° C. on a rotary shaker at 250 rpm for 72 hours until sporulation and cell lysis is observed microscopically releasing the crystals and spores.

A 1.5 ml sample of each whole culture broth is transferred to an Eppendorf centrifuge tube and centrifuged to harvest the crystals and spores. The crystal/spore pellet is washed with 1.0 ml of 1.0M sodium chloride followed by 1.0 ml of deionized water. The pelleted crystals and spores are resuspended in a sodium dextran solution (lower phase). The sodium dextran solution is comprised of 115 μl of deionized water, 120 μl of 20% polyethylene glycol 8000 (DuPont), 170 μl of 20% sodium dextran sulfate, and 50 μl of 3.0M sodium chloride. Then 500 μl of a polyethylene glycol solution (upper phase) is added to the crystal/spore mixture suspended in the lower phase solution. The polyethylene glycol solution is comprised of 30 mg of sodium dextran sulfate, 7.0 g of polyethylene glycol 8000, and 1.75 g of sodium chloride in 100 ml of deionized water. The upper and lower phases are mixed vigorously and allowed to stand for 20 minutes at room temperature until the two phases separate.

The upper phase which contains large quantities of spores is removed with a pipet. The lower phase contains crystals and residual spores. Additional upper phase is added as before and the procedure is repeated until the upper phase contains essentially no detectable spores microscopically. The final lower phase is then diluted with 1.0 ml deionized water and centrifuged to pellet the crystals. The crystal pellet is washed with 1.0 ml of 1.0M sodium chloride followed by 1.0 ml of deionized water. The crystal pellets are finally resuspended in 500 μl of deionized water.

A 50 μl sample of the above crystal suspension is transferred to an Eppendorf centrifuge tube and centrifuged to pellet the crystals. The supernatant is removed and discarded. The pelleted crystals are solubilized by adding 10 μl of deionized water followed by 10 μl of a solubilization buffer and heating the crystal solution for 10 minutes at 100° C. The solubilization solution is comprised of 10 mM Tris-10 mM EDTA-0.15M dithiothretol-2.5% w/v SDS at pH 8.0. The solubilized crystal proteins are analyzed by SDS-PAGE. After SDS-PAGE, the proteins are visualized with Coomassie blue dye.

The inclusions produced by the dipteran-active *Bacillus thuringiensis* isolate EMCC-0110 have a protein with molecular weight of 120 kilodaltons. The inclusions produced by the dipteran-active *Bacillus thuringiensis* isolate EMCC-0111 have proteins with molecular weights of 92 and 40 kilodaltons. The inclusions produced by the dipteran-active *Bacillus thuringiensis* isolate EMCC-0112 have proteins with molecular weights of 92 and 40 kilodaltons. The inclusions produced by the dipteran-active *Bacillus thuringiensis* isolate EMCC-0113 have proteins with molecular weights of 56 and 48 kilodaltons.

EXAMPLE 4

Dipteran activity in whole culture broths from various *Bacillus thuringiensis* isolates The whole culture broths from *Bacillus thuringiensis* isolates EMCC-0110, EMCC-0111, EMCC-0112, and EMCC-0113 as described in EXAMPLE 1 are tested against adult *Drosophila melanogaster* for insecticidal activity using a diet incorporation bioassay.

Specifically, warm artificial insect diet is mixed with diluted whole culture broth to a final concentration of 20%, and then 2.0 ml of the mixture is placed into 13×100 mm tubes and allowed to dry. A control without test sample as well as AVID™ (Merck) as a positive control are also run. Then 8–10 one week old adult *Drosophila melanogaster* are placed into each tube. The tubes are plugged with cotton and incubated at 28°–30° C. After 7–10 days, the tubes are scored for mortality and stunt. The stunt score is the size of the adults on the same day when compared with live, control adults. Stunt scores of 3, 2, 1, and 0 represent the size of the adults as 75%, 50%, 25% of the live, control adults with a rating of 4. A score of 0 represents 100% mortality.

The results from the adult *Drosophila melanogaster* bioassays for the whole culture broths are shown in TABLE 1, infra. The results indicate that all of the whole culture broths have insecticidal activity against adult *Drosophila melanogaster*.

TABLE 1

Adult *Drosophila melanogaster* Activity in Whole Culture Broths

| Strain | Stunt Score |
|---|---|
| Control | 4.0 |
| EMCC-0110 | 0.5 |
| EMCC-0111 | 0.5 |
| EMCC-0112 | 0.5 |
| EMCC-0113 | 0.5 |

EXAMPLE 5

Localization of dipteran activity in whole culture broths of *Bacillus thuringiensis* isolates The location of the dipteran activity, i.e., crystal delta-endotoxin and spores or the supernatant, is determined by bioassay. A 10 ml sample from each of the whole culture broths of *Bacillus thuringiensis* isolates EMCC-0110, EMCC-0111, EMCC-0112, and EMCC-0113 as described in EXAMPLE 1 are centrifuged at 15,000 rpm (Sorvall SS34 rotor) for 15 minutes to separate the supernatant from the pelleted crystal delta-endotoxin and spores. The supernatants are recovered. The crystal/spore mixtures are washed with distilled water and recovered by centrifugation as above.

The same bioassay procedure for adult *Drosophila melanogaster* as described in EXAMPLE 4 is followed.

The crystal delta-endotoxin/spore mixtures from *Bacillus thuringiensis* isolates EMCC-0110, EMCC-0111, EMCC-0112, and EMCC-0113 showed no activity against adult *Drosophila melanogaster*. The results from these bioassays for the supernatants are shown in TABLE 2, infra. All of the supernatants contained insecticidal activity against adult *Drosophila melanogaster*.

TABLE 2

Adult *Drosophila melanogaster* Activity in Supernatants

| Strain | Stunt Score |
|---|---|
| Control | 4.0 |
| EMCC-0110 | 0.5 |
| EMCC-0111 | 0.5 |
| EMCC-0112 | 0.5 |
| EMCC-0113 | 0.5 |

EXAMPLE 6

Purification of dipteran-active substance

*Bacillus thuringiensis* strain EMCC-0110 is fermented and the supernatant recovered as described in EXAMPLE 1. The purification of the dipteran-active substance from the supernatant is achieved using a three step purification procedure. During purification, activity is monitored by an adult *Drosophila melanogaster* bioassay, and purity is determined by capillary electrophoresis as described in EXAMPLE 8. All chromatographic steps are monitored at 278 nm.

Specifically, the bioassay against adult *Drosophila melanogaster* is conducted as follows. Two ml of warm artificial insect diet is placed into 13×100 mm tubes and allowed to dry. 100 $\mu$l of test sample is placed on top of the diet. 1.3× concentrated insect artificial diet is heated to liquid in a microwave oven, and 200 $\mu$l placed on top of the sample. The tube is quickly mixed allowing the sample to mix with the warm 1.3× concentrated artificial insect diet. After the diet/sample mixture on top has dried, then 10–20 adult *Drosophila melanogaster* are placed into each tube. The tubes are plugged with cotton and incubated at 28°–30° C. After 5 days, the tubes are scored for percent mortality.

In step 1, cells, cellular debris, and other insolubles are removed from the whole culture broth of *Bacillus thuringiensis* strain EMCC-0110 as described in EXAMPLE 1 followed by filtration of the resulting supernatant through a 0.2$\mu$ filter. One liter of 0.2$\mu$ filtered supernatant is loaded at 10 ml per minute onto a Baker bonded Octadyl C18 column (2.5×35 cm) which is preconditioned with 100% acetonitrile and then pre-equilibrated with 5% acetonitrile in deionized water. Following loading, the column is washed at 10 ml per minute with 250 ml of deionized water. The pass-through is collected (approximately 1250 ml) and bioassayed for activity.

In step 2, the pass-through from step 1 is diluted to 2000 ml with deionized water. 1.21 g of Trizma® Base (Sigma Chemical Co.) is added to a final concentration of 5 mM. The solution is then adjusted to pH 8.0. A sample of 1000 ml of the solution is loaded at 8.0 ml per minute onto a Pharmacia Q-Sepharose fast flow column (2.5 cm×30 cm) which is pre-equilibrated with 20 mM Tris pH 8.0. The column is then washed at 8.0 ml per minute with 20 mM Tris-HCl pH 8.0 for 1–2 column volumes, and then eluted with a 1.5 liter continuous gradient from 20 mM Tris-HCl pH 8.0 to 20 mM Tris-HCl-0.5M sodium chloride pH 8.0. Fractions of 16.0 ml are collected, bioassayed, and examined for purity. The active fractions are pooled (approximately 200 ml), lyophilized to dryness, and redissolved in deionized water to 1/20 to 1/50 the original volume.

In step 3, a 5.0 ml sample of the 20× concentrated pool from step 2 is loaded at 1.4 ml per minute onto a Pharmacia Sephadex G-25 column (1.6 cm×80 cm) which is pre-equilibrated with deionized water. The column is eluted at 1.4 ml per minute with deionized water. Fractions of 3.0 ml are collected, bioassayed and examined for purity. The active fractions are pooled (approximately 30 ml) and dried by lyophilization.

Capillary electrophoresis showed that the substance of the present invention is purified to approximately 98% purity by the above three step purification procedure.

The purified substance is soluble in water, is stable at a pH of between about 2 and about 12 in water for 10 days, is stable in water at about 72° C. for at least about 60 minutes, is less than 1000 in molecular weight, and has UV maxima at 230 and 262 nm (pH 7.0). β-exotoxin type I has UV maxima at 227 and 259 nm (pH 7.0) while β-exotoxin type II has UV maxima at 230 and 262 nm (pH 7.0).

EXAMPLE 7

Dipteran-active substance structural data

Structural data on the substance of the present invention is obtained from spectroscopic information collected on the purified compound from EXAMPLE 6.

Mass spectral data on the compound shows a molecular weight of 758 with a fragment ion of 679. β-exotoxin type I has a molecular weight of 701. Mass spectral data on β-exotoxin type II reveals that the largest frament ion has a mass of 481.

NMR data collected on the compound indicated it is a uracil nucleoside with three sugar moieties and two phosphates with $^1$H-NMR chemical shifts at 7.62 (1H, d), 5.83 (1H, d), and 5.78 (1H, d) (see FIG. 1, TABLES 3 and 4). The compound differs significantly from β-exotoxin type I (see FIG. 2) and β-exotoxin type II. β-exotoxin type I is an adenine nucleoside while β-exotoxin type II is a pseudoureido nucleoside with only one proton on the nucleoside base (Levinson, in Hickle and Finch (eds.), *Analytical Chemistry of Bacillus thuringiensis*, ACS Symposium Series, Washington, D.C., 1990, pp. 114–136).

TABLE 3

Structural Data on Dipteran-Active Substance

| | Proton Chemical Shifts (ppm) | | |
|---|---|---|---|
| | Substance | β-exotoxin type I | β-exotoxin type II |
| Nucleoside Base | 7.62(1H, d)<br>5.78(1H, d) | 8.34(1H, s)<br>8.14(1H, s) | 7.95(1H, d) |
| Ribose 4' Proton | 5.83(1H, d) | 5.90(1H, d) | | s = singlet
d = doublet

TABLE 4

$^1$H AND $^{13}$C DATA OF DIPTERAN-ACTIVE SUBSTANCE

| Position | $^1$H NMR (ppm) | $^{13}$C NMR (ppm) |
|---|---|---|
| 1 | | 166.5 |
| 2 | 5.78(d, J=8.2Hz) | 102.9 |
| 3 | 7.63(d, J=8.2Hz) | 142.1 |
| 4 | | |
| 5 | | 152.3 |
| 6 | | |

TABLE 4-continued

¹H AND ¹³C DATA OF DIPTERAN-ACTIVE SUBSTANCE

| Position | ¹H NMR (ppm) | ¹³C NMR (ppm) |
|---|---|---|
| 1' | 5.83(d, J=5.4) | 88.8 |
| 2'–5' | 3.7–4.4(multiple peaks) | 70–78 |
| 1" | 4.8(d, J=3.76) | 96.8 |
| 2"–6" | 3.2–3.7(multiple peaks) | 50–65 |

6 other hydroxyl containing carbons between 3.3–3.6 corresponding to carbon signals between 60–70 ppm.

EXAMPLE 8

Quantitation of substance with dipteran activity

*Bacillus thuringiensis* strain EMCC-0110 is fermented as described in EXAMPLE 1. The quantitation of the amount of the substance of the present invention in the fermentation broth is determined by capillary electrophoresis.

Specifically, a Biorad Biofocus 3000 Capillary Electrophoresis System equipped with a 50 μm×36 cm uncoated capillary, 0.1M Tris-Borate-0.0002M EDTA pH 8.3, voltage at 20 KV, positive to negative polarity, and UV detection at 260 nm. The analysis time is 10 minutes for the substance of the present invention eluting at 5.2 minutes.

Supernatant from the fermentation described in EXAMPLE 1 is recovered by centrifugation, filtered through a 0.2μ filter, and analyzed by capillary electrophoresis as described above. The results indicated that the substance of the present invention is present at a level of approximately 0.2 g per liter broth.

EXAMPLE 9

Activity against *Musca domestica* larvae

*Bacillus thuringiensis* strain EMCC-0110 is grown in the medium as described in EXAMPLE 1. The supernatant containing the substance of the present invention is recovered from the whole broth as described in EXAMPLE 1. Samples for bioassay are prepared as follows: (1) Undiluted supernatant, (2) 5 ml water plus 10 ml (1), (3) 5 ml water plus 10 ml (2), (4) 5 ml water plus 10 ml (3), (5) 5 ml water plus 10 ml (4), (6) 5 ml water plus 10 ml (5) and (7) 5 ml water plus 10 ml (6).

*Musca domestica* (house fly) larvae are reared from eggs in CSMA standard fly larva medium (Purina Mills #5060) for 3 days at 30° C. 19 g of freshly prepared CSMA medium are weighed into 4 oz specimen cups. One ml of each test sample is added to the medium and stirred thoroughly with a metal spatula. The cups are capped and allowed to sit for 2 hours. Twenty-five *Musca domestica* larvae are transferred to each cup. Each cup is covered with 32-mesh nylon chiffon and held in place with a rubber band. Three replicates and a control (sterile water) are assembled for each dilution. Each assay is incubated for 14 days at 28° C.

After 14 days, the number of adult *Musca domestica* are counted in each cup. Percent of control mortality is determined as the number of adult *Musca domestica* divided by the number of larvae placed in the cup (%CM). The results are presented in TABLE 4, infra, and indicate the supernatant is insecticidal against *Musca domestica* larvae.

TABLE 4

Activity against *Musca domestica* larvae

| Sample Conc. (ug/g) | # Adults | % CM |
|---|---|---|
| 50,000 | 7/75 | 86.5 |
| 33,333 | 26/75 | 50.0 |
| 22,222 | 31/75 | 40.4 |
| 14,815 | 31/75 | 40.4 |
| 9,877 | 37/75 | 28.8 |
| 6,584 | 56/75 | 0 |
| 4,390 | 51/75 | 1.9 |
| Control | 52/75 | — |

EXAMPLE 10

Potentiation of Insecticidal Activity of *Bacillus thuringiensis* subsp. kurstaki

*Bacillus thuringiensis* strain EMCC-00110 is grown in the medium as described in EXAMPLE 1. Purified dipteran-active substance of the present invention is obtained as described in EXAMPLE 6.

The potentiation of the pesticidal activity of a BIOBIT™FC crystal delta-endotoxin by the dipteran-active substance is determined by artificial diet incorporation bioassay using second instar *Spodoptera exigua* larvae.

Standard artificial diet composed of water, agar, sugar, casein, wheat germ, methyl paraben, sorbic acid, linseed oil, cellulose, salts, and vitamins are prepared in a 20 liter kettle. Aliquots of 1.0 ml are dispensed with a pipettor into a plastic tray bearing 240 individual wells and allowed to solidify.

A 1 mg/ml stock solution (20 ml) BIOBIT™FC (Novo Nordisk A/S) at a potency of 8 BIU/mg is made in a dilute agar solution composed of 1.7 g of agar (Difco) per liter deionized water. The 1 mg/ml stock solution is then diluted with the agar solution to make 0.25, and 0.12, and 0.06 mg/ml dilutions (40 ml each). A control of agar solution without BIOBIT™FC is also prepared. A 3.0 ml aliquot of each of the four doses is dispensed with a Hamilton pipettor into the individual wells at a rate of 10 wells per dose.

A 0.4 mg/ml solution of the substance of the present invention is prepared by dissolving 4 mg of the substance of the present invention in 10 ml of deionized water. A 50 μl aliquot of the substance of the present invention solution is dispensed into each well with a pipettor, shaken to mix with the BIOBIT™FC solution, and then allowed to dry overnight.

One 2nd instar larva of *Spodoptera exigua* is added to each well, and then the trays are covered with a perforated sheet of clear mylar. The trays are incubated for four days at 28° C. and 65% relative humidity. After four days, the number of live larvae per 10 wells is rated.

The results, as shown in TABLE 5, infra, demonstrate that the dipteran-active substance of the present invention potentiates the insecticidal activity of BIOBIT™FC crystal delta-endotoxin.

TABLE 5

Potentiation of BIOBIT ™ FC

| BIOBIT ™ FC Dose (mg/ml) | Control | Number of Live Larvae Substance |
|---|---|---|
| 0 | 10 | 10 |
| 0.06 | 10 | 4 |
| 0.12 | 10 | 3 |
| 0.25 | 10 | 4 |

DEPOSIT OF MICROORGANISMS

The following strains of *Bacillus thuringiensis* have been deposited according to the Budapest Treaty in the Agricultural Research Service Patent Culture Collection, Northern Regional Research Laboratory (NRRL), 1815 University Street, Peoria, Ill., 61604, USA.

| Strain | Accession Number | Deposit Date |
|---|---|---|
| EMCC-0110 | NRRL B-21269 | May 27, 1994 |
| EMCC-0111 | NRRL B-21270 | May 27, 1994 |
| EMCC-0112 | NRRL B-21271 | May 27, 1994 |
| EMCC-0113 | NRRL B-21272 | May 27, 1994 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A substance having the following properties: (a) pesticidal activity against an insect pest of the order Diptera; (b) acts together with a Bacillus related pesticide; and (c) is a uracil nucleoside with three sugar moieties and two phosphates and $^1$H-NMR chemical shifts at about 7.62 (1H,d), 5.83 (1H,d), and 5.78 (1H,d).

2. The substance according to claim 1 wherein said substance has a molecular weight of less than about 1000.

3. The substance according to claim 1 wherein the substance is obtainable from a supernatant of a Bacillus fermentation in which essentially all of the pesticidal activity of said strain is in the supernatant of said fermentation.

4. The substance according to claim 3 wherein the substance is obtainable from a supernatant of a *Bacillus thuringiensis* fermentation.

5. The substance according to claim 3 in which the substance is obtainable from a biologically pure culture of a *Bacillus thuringiensis* strain selected from the group consisting of EMCC-0110, EMCC-0111, EMCC-0112, and EMCC-0113, and mutants and variants thereof, which are capable of producing the substance.

* * * * *